US008993247B2

(12) United States Patent
Shanahan et al.

(10) Patent No.: US 8,993,247 B2
(45) Date of Patent: Mar. 31, 2015

(54) ASSAY FOR VASCULAR CALCIFICATION

(75) Inventors: Catherine M. Shanahan, London (GB); Alexander N. Kapustin, London (GB)

(73) Assignee: King's College London, London (GB)

( * ) Notice: Subject to any disclaimer, the term of this patent is extended or adjusted under 35 U.S.C. 154(b) by 0 days.

(21) Appl. No.: 13/577,978

(22) PCT Filed: Feb. 11, 2011

(86) PCT No.: PCT/GB2011/050258
§ 371 (c)(1),
(2), (4) Date: Oct. 5, 2012

(87) PCT Pub. No.: WO2011/098825
PCT Pub. Date: Aug. 18, 2011

(65) Prior Publication Data
US 2013/0017562 A1 Jan. 17, 2013

(30) Foreign Application Priority Data
Feb. 12, 2010 (GB) ................................. 1002382.8

(51) Int. Cl.
*G01N 33/53* (2006.01)
*G01N 33/68* (2006.01)
(52) U.S. Cl.
CPC ...... *G01N 33/6893* (2013.01); *G01N 2800/323* (2013.01)
USPC ............................................ 435/7.1; 435/7.2
(58) Field of Classification Search
None
See application file for complete search history.

(56) References Cited

U.S. PATENT DOCUMENTS

| 2003/0027211 | A1* | 2/2003 | Price | ............................... | 435/7.1 |
| 2008/0273206 | A1 | 11/2008 | Genge et al. | | |
| 2008/0280847 | A1 | 11/2008 | Giachelli et al. | | |

OTHER PUBLICATIONS

Price II (JBC 2003, vol. 278, p. 22153).*
Kundranda et al. (Biochim Biophy Acta 2004 vol. 1693, p. 111).*
Collett, Georgina et al.; "Axl/Phosphatidylinositol 3-Kinase Signaling Inhibits Mineral Deposition by Vascular Smooth Muscle Cells"; Circulation Research 2; Mar. 2007; pp. 502-509; with Online Supplement (6 pages); XP002629505.
Irabarren, C., MD, MPH, PhD; "Relationship between arterial vascular calcifications seen on screening mammograms and biochemical markers of endothelial injury"; Breast Diseases: A Yearbook Quarterly, vol. 20. No. 3; Jan. 2009; pp. 281-282; XP026599998.
Kapustin, Alexander et al.; "Targeting vascular calcification: softening-up a hard target"; Current Opinion in Pharmacology; vol. 9, No. 2; Apr. 2009; pp. 84-89.
Kullich, Werner et al.; "Matrix-Gla-Protein, a Marker of Vascular Calcification, in Hyperlipidemia"; Wiener Medizinische Wochenschri Ft, Springer-Verlag, AT; vol. 153, No. 15-16; Aug. 2003; pp. 360-364; XP019379686; Abstract translated into English.
Pidal, Diego et al.; "Relationship between arterial vascular calcifications seen on screening mammograms and biochemical markers of endothelial injury"; European Journal of Radiology, vol. 69, No. 1; Jan. 2009; pp. 87-92; XP025874958.
Proudfoot, Diane et al.; "Apoptosis Regulates Human Vascular Calcification In Vitro Evidence for Initiation of Vascular Calcification by Apoptotic Bodies"; Circulation Research, vol. 87; Nov. 2000; pp. 1055-1062.
Reynolds, Joanne L. et al.; "Human Vascular Smooth Muscle Cells Undergo Vesicle-Mediated Calcification in Response to Changes in Extracellular Calcium and Phosphate Concentrations: A Potential Mechanism for Accelerated vascular Calcification in Esrd"; J Am Soc Nephrol 15; Nov. 2004; pp. 2857-2867.
Shao, Jian-Su et al.; "Molecular Mechanisms of Vascular Calcification: Lessons Learned from the Aorta"; Arterioscler Thromb Vasc Biol; Jul. 2006; pp. 1423-1430.
Shroff, Rukshana C. et al.; "The Vascular Biology of Calcification"; Semin. Dialysis, vol. 20, No. 2; Mar.-Apr. 2007; pp. 103-109.
Shroff, Rukshana C. et al.; "Dialysis Accelerates Medial Vascular Calcification in Part by Triggering Smooth Muscle Cell Apoptosis"; Circulation, 118 (17); Oct. 2008; pp. 1748-1757.
Son, Bo-Kyung et al.; "Statins Protect Human Aortic Smooth Muscle Cells from Inorganic Phosphate-Induced Calcification by Restoring Gas6-Axl Survival Pathway"; Circulation Research, vol. 98, No. 8; Apr. 2006; pp. 1024-1031; with Online Supplement (13 pages); XP002629506.
Théry, Clotilde et al.; "Exosomes: Composition, Biogenesis and Function"; Nature Reviews—Immunology; vol. 2; Aug. 2002; pp. 569-579.
Trion, Astrid, MSc et al.; "Vascular smooth muscle cells and calcification in atherosclerosis"; Am. Heart J., vol. 147, No. 5; May 2004; pp. 808-814.
International Search Report mailed May 24, 2011 for International Application No. PCT/GB2011/050258.
International Preliminary Report on Patentability and Written Opinion of the International Searching Authority issued Aug. 14, 2012 for International Application No. PCT/GB2011/050258.

* cited by examiner

*Primary Examiner* — Jacob Cheu
(74) *Attorney, Agent, or Firm* — Brinks Gilson & Lione

(57) ABSTRACT

An assay for identifying an individual having or at risk of developing vascular calcification, said assay comprising obtaining a blood sample from an individual and measuring the level of a vesicular compound in a matrix vesicle present in the blood sample from said individual; wherein an increased level of said compound indicates an individual at risk of developing vascular calcification.

18 Claims, 17 Drawing Sheets

Figure 1:
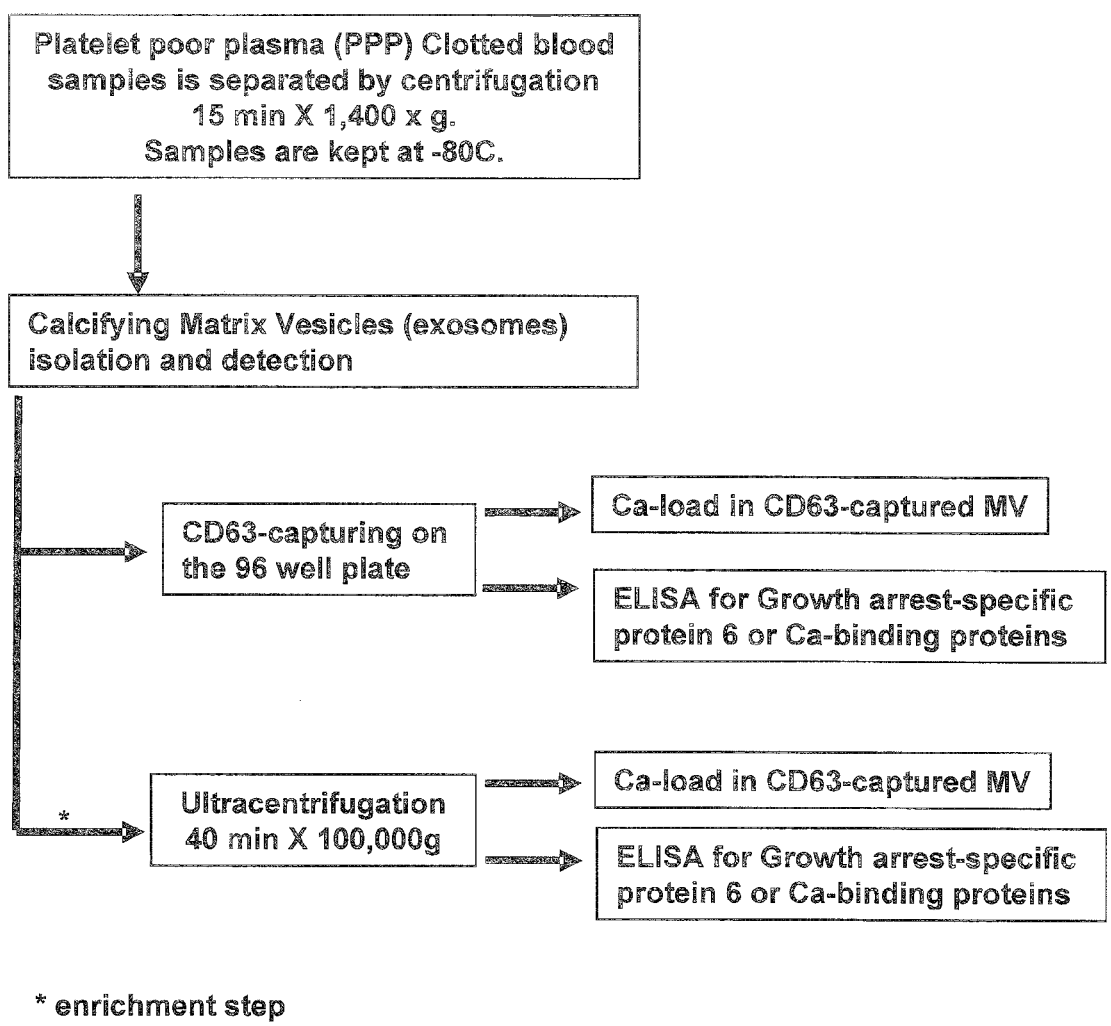

Figure 1. Schematic of the processing steps for the isolation of matrix vesicles from human blood and the detection of matrix vesicle components.

Figure 2:
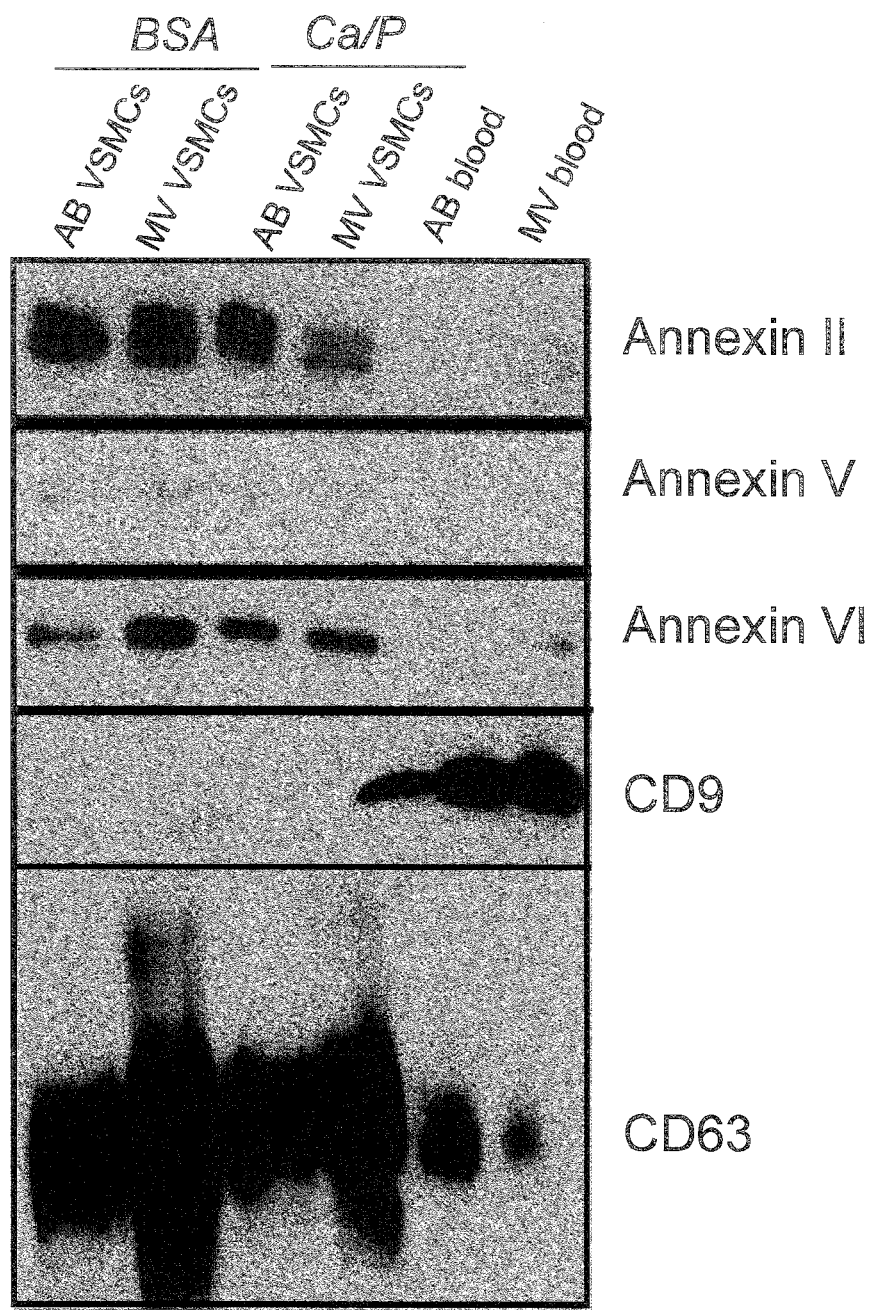

Figure 2: Markers enriched in VSMCs-derived matrix vesicles were also detected in matrix vesicles isolated by ultracentrifugation of human blood.

Figure 3:
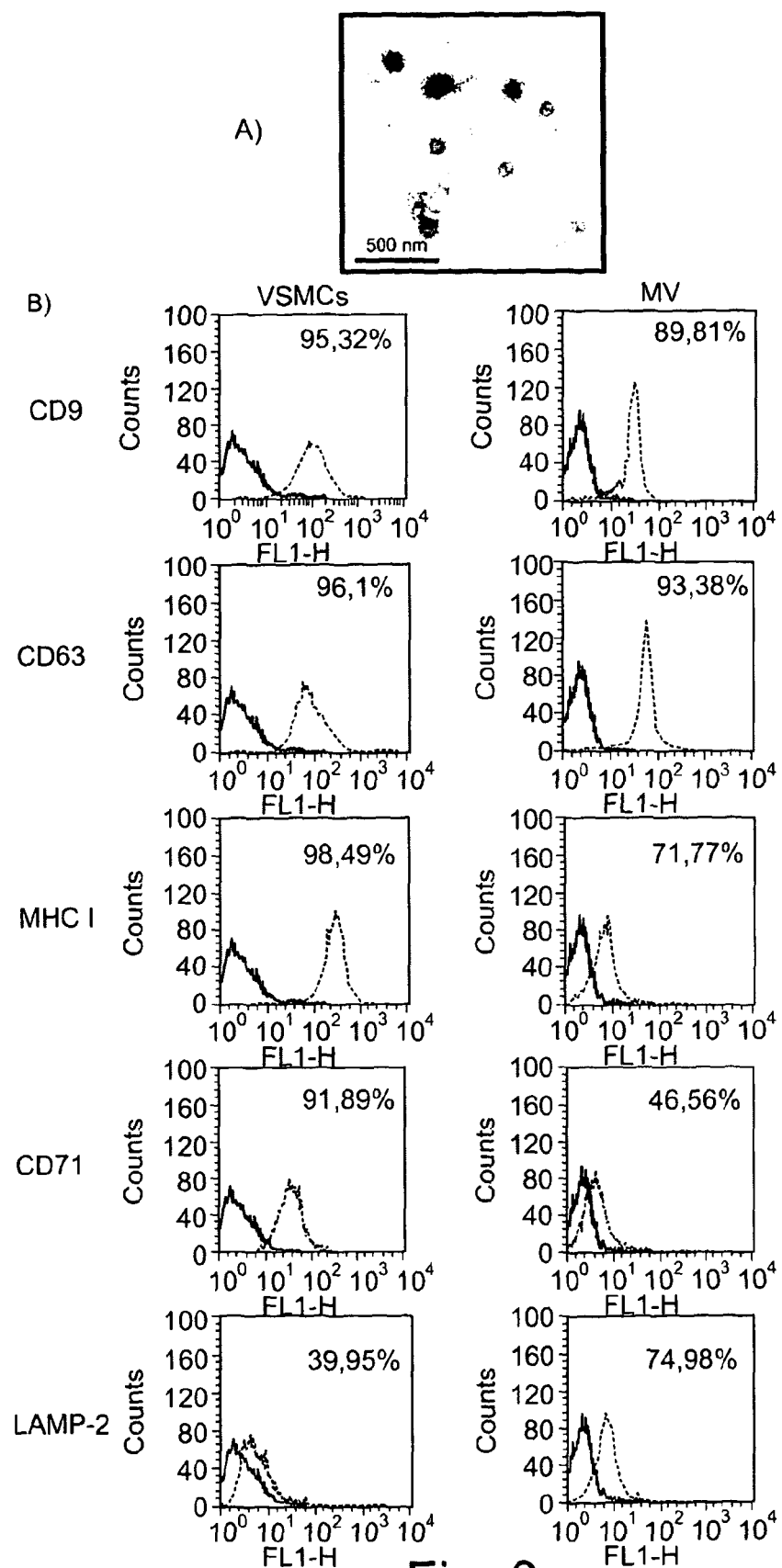

C)
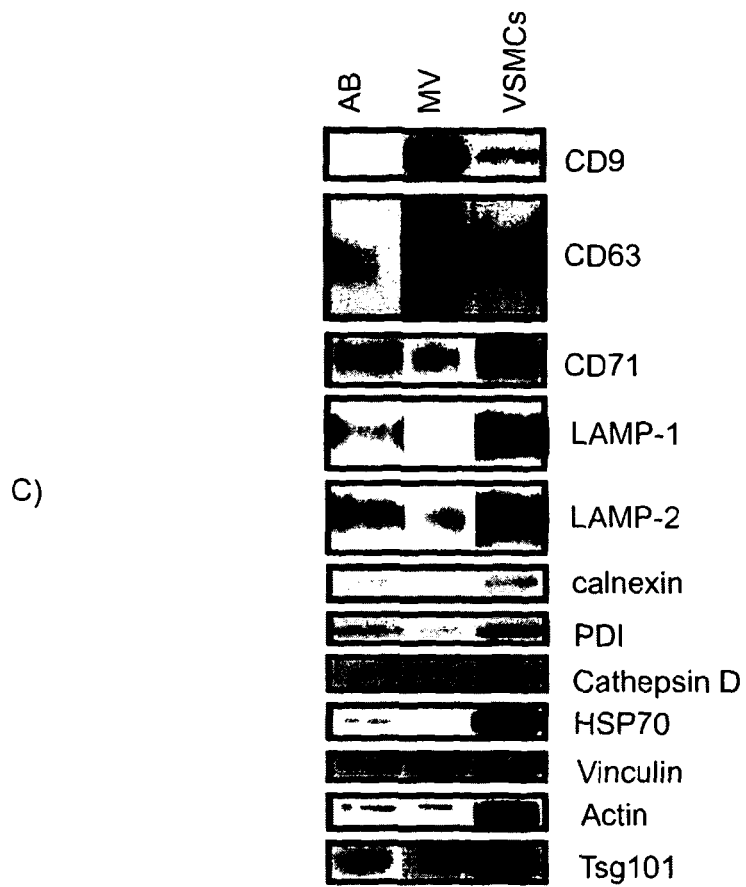
D)
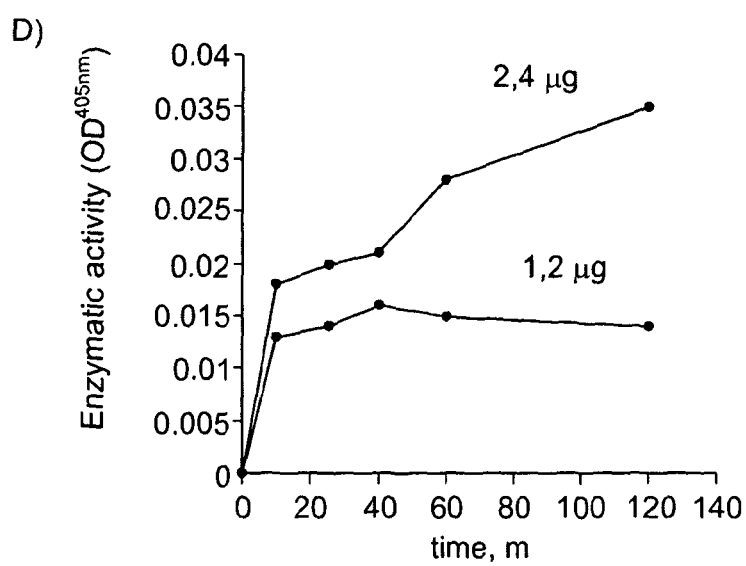
Fig. 3 cont.

Figure 4
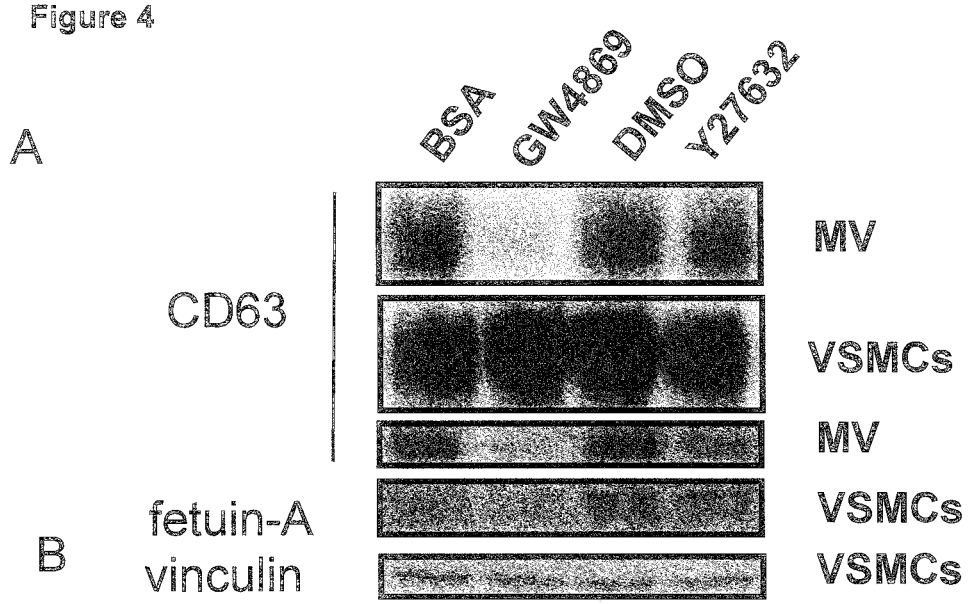
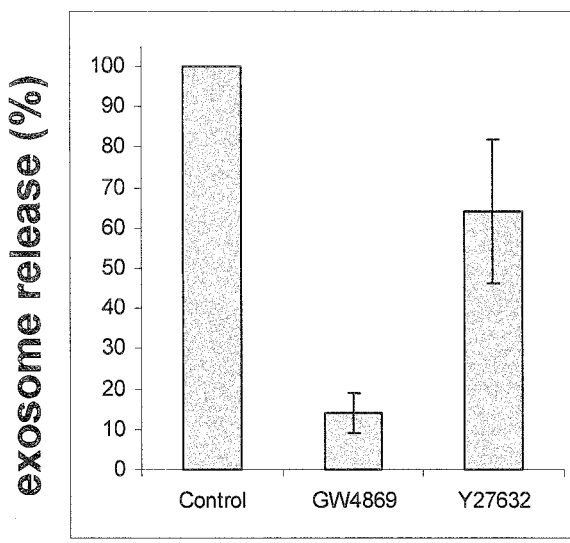

Figure 5
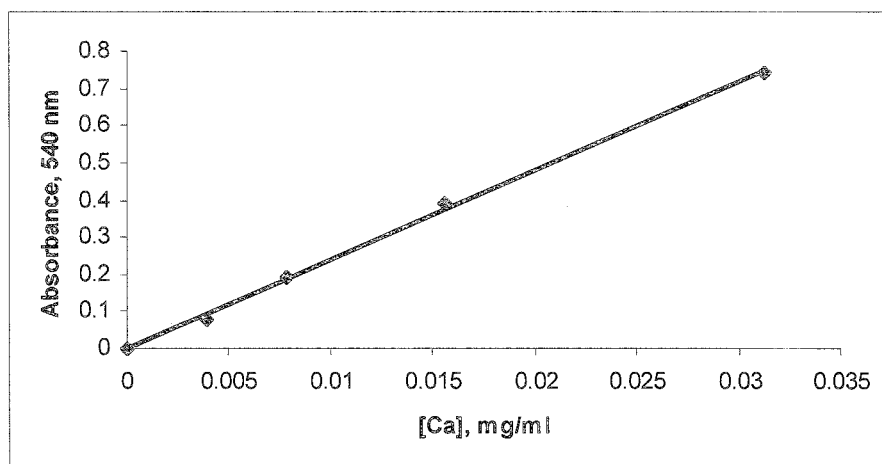
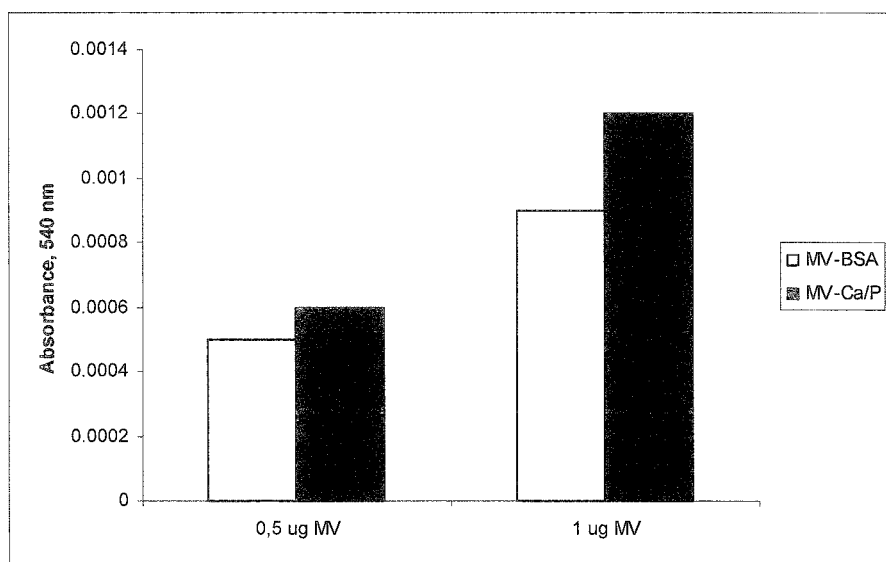

Figure 6:
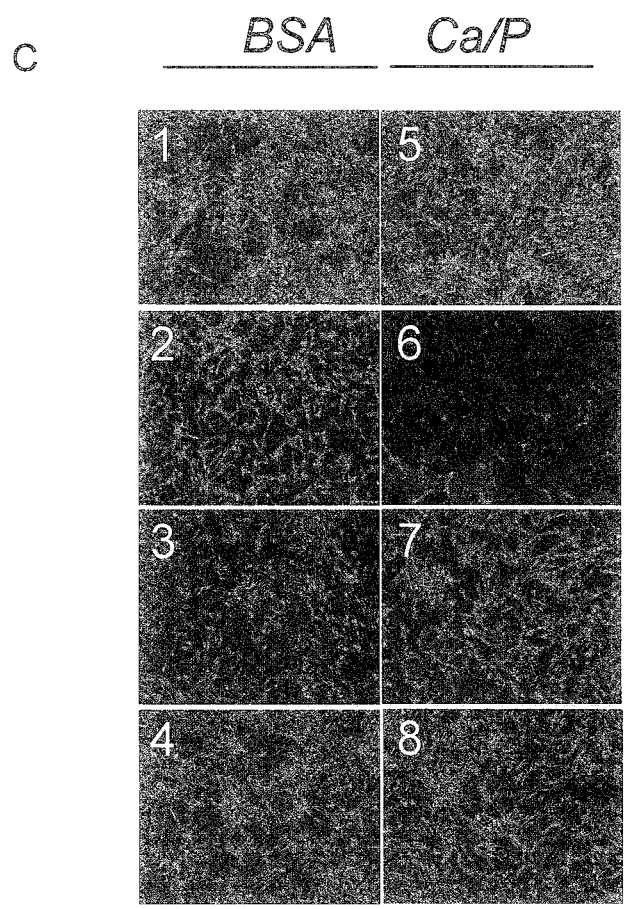

Figure 6
A
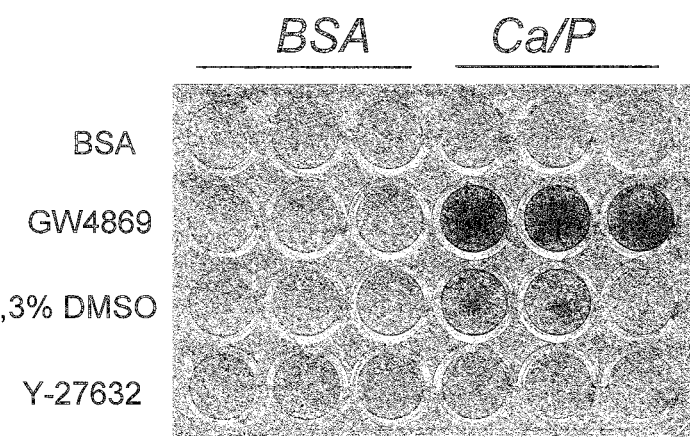
B
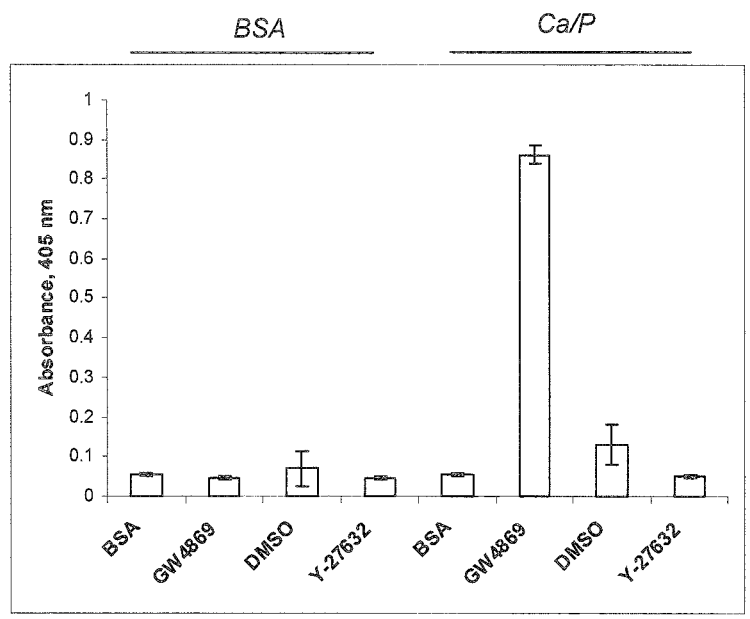

Figure 8
Normal uncalcified aorta
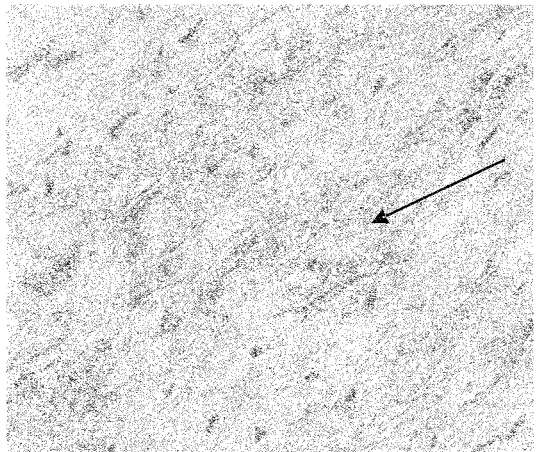
Calcified aorta (media)
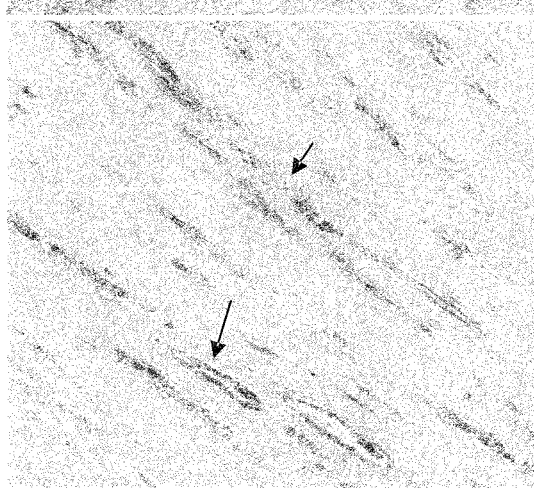
Calcified aorta (intima)

ASSAY FOR VASCULAR CALCIFICATION

This application claims the benefit under 35 U.S.C. §371 of International Application No. PCT/GB2011/050258, filed Feb. 11, 2011, which claims the benefit of Great Britain Patent Application No. 1002382.8, filed Feb. 12, 2010, which are incorporated by reference herein in their entirety.

FIELD OF INVENTION

The present invention relates to an assay for the detection and diagnosis of vascular calcification linked to cardiovascular disease.

BACKGROUND

It is has been established that vascular calcification can cause stiffening of the vascular wall, reducing its compliance and lead to ventricular hypertrophy (thickening of the heart wall with reduced pumping ability), inadequate supply of blood and oxygen to the heart and heart attack. Vascular calcification is an increasingly important clinical problem particularly in the context of renal disease and diabetes type 2. It is caused by the deposition of calcium phosphate salt crystals, in the intima and/or media of arteries, with calcification at both sites common in renal disease. Calcification at either site is correlated with poor cardiovascular outcomes. Intimal calcification occurs almost ubiquitously with atherosclerosis. It's quantification using multi-slice CT scanning provides an accurate measure of atherosclerotic load that can be used to predict a patient's risk for myocardial infarction. Calcification might be involved in mechanical disruption of the plaque and may also promote inflammation by direct interactions between plaque cells and calcium nanocrystals. Medial calcification has now been identified as a major factor contributing to the high cardiovascular mortality in patients with renal failure and diabetes. It reduces arterial compliance, particularly in the aorta, leading to poor cardiac perfusion and associated heart failure. It is currently known that cardiovascular disease accounts for 48-50% of death among adults undergoing regular dialysis and patients with type 2 diabetes [USRDS 2008 Annual Data Report].

Currently available methods for the detection of vascular calcification such as plain X-ray or cardiac computed tomography (CT) scans are not sensitive enough to measure early vascular calcium load. Therefore, the existing approaches are only effectively used for patients with severe calcification, where further treatment is difficult.

The inventors have discovered that both developmental osteogenesis and arterial wall calcification is initiated by cell-derived, mineralization competent vesicles. Calcification is initiated by release from living vascular smooth muscle cells (VSMCs) of membrane-bound matrix vesicles (MV) and also by apoptotic bodies from dying cells. Vesicles released by VSMCs after prolonged exposure to Ca and P contained preformed basic calcium phosphate and calcified extensively. Importantly, in MV analysed by proteomic mass spectroscopy it was found that MV composition is regulated by VSMCs and is dependent on the environment. For example, MV released under normal physiological conditions do not calcify because they are loaded with mineralization inhibitors derived from VSMCs (matrix Gla protein) and serum (fetuin-A). Perturbation of the production or function of these inhibitors, due to different stresses and/or inflammation leads to accelerated vascular calcification. In addition, in a calcified environment, VSMCs undergo osteo/chondrocytic conversion, expressing transcription factors including Runx2 and osterix, as well as matrix proteins, which are normally restricted to bone (Reynolds J L et al., J Am Soc Nephrol. 2004 November; 15(11):2857-67; Shroff R C et al., Circulation; 2008, Oct. 21; 118(17):1748-57; Kapustin A and Shanahan C M. Curr Opin Pharmacol. 2009 April; 9(2):84-9).

SUMMARY OF THE INVENTION

The present invention is based on the inventors surprising discovery that matrix vesicles originating from vascular smooth muscle cells as well as being present in the vessel wall are also present in the blood of individuals. They have further identified that there is a correlation between the levels of certain vesicular compounds in the matrix vesicles present in the blood of an individual and that individual's risk of having or of developing vascular calcification.

In light of this discovery the inventors have developed a diagnostic assay to determine the levels of these vesicular compounds in the circulating matrix vesicles as an early indicator of vascular calcification or the risk of an individual developing vascular calcification potentially leading to, for example, cardiovascular disease.

Therefore, in one aspect the present invention provides an assay for identifying an individual having or at risk of developing vascular calcification, said assay comprising the steps of:—
obtaining a blood sample from said individual; and
measuring the amount of a vesicular compound associated with a matrix vesicle present in the blood sample;
wherein an increased amount of said compound indicates an individual having or at risk of developing vascular calcification.

According to a second aspect of the present invention there is provided a method of identifying an individual having or at risk of developing vascular calcification comprising:
i) obtaining a blood sample comprising matrix vesicles isolated from said individual;
ii) measuring the amount of a vesicular compound associated with said matrix vesicles;
wherein an increased amount of said vesicular compound indicates that the individual has or is at risk of developing vascular calcification.

DETAILED DESCRIPTION OF THE INVENTION

It will be apparent to one skilled in the art that the degree of vascular calcification present in an individual or patient is correlated with the risk of the individual developing a cardiovascular disorder. More particularly with the risk of artherosclerosis; intermittent claudication and lower limb ischemia; hypertension; myocardial infarction (heart attack) and/or heart failure.

In the present invention, the matrix vesicles are preferably matrix vesicles (MV) derived from vascular smooth muscle cells (VSMCs).

The skilled person will understand that vascular smooth muscle cell (VSMCs) matrix vesicles are membrane-enclosed vesicles secreted by smooth muscle cells. These contain calcium and phosphate as well as a range of cellular proteins originating from the cytosol, plasma membrane, nucleus, mitochondria, endosomes, Golgi and proteosomes. MV are able to accumulate calcium from the extravesicular media resulting in calcium phosphate precipitation.

As used herein, it will be understood that the term "having or at risk of developing vascular calcification" refers to an individual having an identifiable level of vascular calcification or an individual who may or may not have a low level of vascular calcification which is not identifiable by conventional means, but who is at risk of developing an identifiable level of vascular calcification.

As used herein, it will be understood that the term "increased amount" means that the matrix vesicles contain a higher amount or concentration of the vesicular compound when compared to the normal range seen in the general population not having or at risk of developing vascular calcification.

In some preferred embodiments, the vesicular compound will not be present in matrix vesicles isolated from individuals who do not have or are not at risk of developing vascular calcification.

It will be understood that the vesicular compound may be an intra-vesicular compound e.g a compound found in the lumen of the matrix vesicle, or a compound associated with a matrix vesicle by, for example, attachment to the vesicle surface.

In preferred embodiments, the increased amount refers to a level which is at least 10%, 20%, 30%, 40%, 50%, 60%, 70%, 80%, 90%, 100%, 150%, 200%, 300%, 400% or 500% higher than the normal range of the vesicular compound. More preferably, at least 100% higher than the normal range of the vesicular compound It will be apparent to the skilled person that the normal range may differ for each vesicular compound. The normal range can be considered to be the range present in individuals who do not show any signs of vascular calcification or do not fall into an at risk group, for example, individuals having a chronic renal disorder or type 2 diabetes.

It will be understood that the blood sample for use in the assay and method of the present invention has been previously obtained from the individual.

As used herein the term blood sample includes whole blood samples and also samples comprising blood components, such as, for example, plasma containing matrix vesicles isolated from a whole blood sample. In a preferred embodiment, the sample is isolated from the individual prior to the assay or method of the present invention being performed.

It will be apparent that the matrix vesicles for use in the assay and method of the invention are those matrix vesicles present in the blood of an individual.

It will be readily apparent that the assay of the invention is an in vitro assay performed on matrix vesicles which have previously been isolated from an individual.

In a further preferred embodiment, the matrix vesicles are isolated from the sample. It will be readily apparent that the matrix vesicles can be isolated from the sample by any suitable means. In one preferred embodiment they are captured using antibodies. In another preferred embodiment, the matrix vesicles are isolated by ultracentrifugation.

It will be readily apparent that any suitable antibody against a matrix vesicle antigen can be used to capture the matrix vesicles, for example, the antibody may be selected from the non exhaustive list comprising an antibody against CD63, T-cadherin, CD166 or Annexin A6 or at least one of the proteins listed in Table 2 below. Preferably, said antibody is a monoclonal antibody. Most preferably, the antibody is an antibody against a matrix vesicle specific epitope.

In a most preferred embodiment the antibody is an anti CD63 antibody.

As used herein the term individual refers to a human or other animal. In a preferred embodiment, the individual is human. In a more preferred embodiment, the individual is an individual suffering from a chronic renal disorder and/or from atherosclerosis and/or from type 2 diabetes. The terms individual and patient are used interchangeably herein, unless specifically stated otherwise or obviously otherwise due to context.

It will be understood that the vesicular compound may be one or more specific proteins and/or one or more mineral salt, for example, a calcium salt, phosphate salt and/or a calcium phosphate salt.

In preferred embodiments, the vesicular compound is selected from at least one of calcium, hydroxyapatite, a calcium salt, a phosphate salt and/or a calcium phosphate salt or at least one protein as defined in Table 3 below or at least one of Gas6; Microtubule-associated protein 1B; Thy-1 membrane glycoprotein; 60S ribosomal protein L30, L27a; Prohibitin; Proteasome subunit beta type-4; Elongation factor 1-delta; Gremlin-1; 14-3-3 protein beta/alpha; COP9 signalosome complex subunit CSN4; Ezrin; Programmed cell death 6-interacting protein; CD109; Protein kinase C delta-binding protein; Calmodulin; Nucleolin, PAI-1, MMP-14

Preferably, the compound is calcium, calcium phosphate salts, hydroxyapatite or Growth arrest-specific protein 6.

It will be further understood that the amount of the vesicular compound present in the sample can be measured as an absolute value (for example in µg) or as a concentration (for example µg/µl).

It will be understood that the amount of vesicular compound present in the matrix vesicle can be measured by any suitable means. Said means may depend upon the compound being measured. The skilled person will be readily aware of such means which in preferred embodiments can be spectrophotometry, fluorescence spectroscopy, western blotting, $Ca^{45}$ uptake, flow cytometry, confocal laser scanning microscopy, ELISA or quantitative PCR.

In one embodiment the assay according to the present invention can be used for the quantitative determination of total calcium in matrix vesicles in blood samples of patients suffering from a disorder which places them at risk of developing vascular calcification, for example, chronic kidney disease, artherosclerosis and diabetes type 2.

In an alternative embodiment of the present invention, the assay or method can be used to predict and evaluate vascular damage in different cardiovascular diseases using markers of VSMCs damage that are expressed on VSMCs and VSMCs-derived vesicles. For example, the following markers have been shown to increase in vessels from patients undergoing dialysis (Shroff R C et al., Circulation, 2008), and can be tested by ELISA or qPCR performed on vesicles isolated from the patient's blood sample in order to predict vascular wall damage in patients with, for example, chronic kidney disease and type 2 diabetes: alkaline phosphatase activity (enzyme, involved in the generation of phosphorus, spectrophotometrical detection); Runx2 (osteogenic transcription factor, detection by qPCR); osterix (osteogenic transcription factor, detection by qPCR) armexin VI (calcium-binding protein, detection by ELISA); fetuin-A (serum calcium-binding protein, detection by ELISA); matrix Gla-protein (internal calcium-binding protein, detection by ELISA).

EXAMPLES

The invention will now be further described with reference to the following figures in which:—

FIG. 1 shows a schematic representation of a method of performing the assay of the present invention.

FIG. 2 shows detection of the common markers (CD63, CD9, annexin II, annexin V and annexin VI) in the matrix vesicles, isolated by ultracentrifugation from human smooth muscle cells and matrix vesicles isolated by ultracentrifugation from human blood as detected by western blot. AB, Apoptotic bodies; MV, matrix vesicles. VSMCs were treated with BSA (control) or with calcium and phosphate (Ca/P); Platelet poor plasma were isolated from the patient's blood by 1400×g centrifugation, apoptotic bodies were isolated by 2500×g centrifugation and matrix vesicles were obtained from the supernatant by 100000×g centrifugation.

FIG. 3 shows a characterization of matrix vesicles, isolated from human smooth muscle cells.

A—Electron microscopy: showing size and morphology typical of matrix vesicles/exosomes.

B—flow cytometry analysis; showing surface exposure of markers on VSMCs and MV, immobilized to 4 μm latex beads.

C—western-blotting; showing differential expression of markers in MV compared with apoptotic bodies (AB) and VSMCs lysates.

D—acetylcholinesterase activity: MV were isolated from VSMCs and incubated with acetylthiocholine and 5,5'-dithio-bis(2-nitrobenzoic acid) and the activity of acetylcholinesterase, which is known to be presented on exosomes (Savina et al., 2002), was assayed by spectrophotometer.

FIG. 4 A shows an inhibition of matrix vesicles release by human smooth muscle cells by GW4869 indicated by absence of matrix vesicle markers (CD63 and Fetuin A) in MV lysates. Panel B, quantification of matrix vesicle release by VSMCs was performed using densitometry analysis of CD63, presented in MV as defined by western-blot analysis (shown in A). Mean±SD, n=3.

FIG. 5 shows quantification of calcium in matrix vesicles isolated from human smooth muscle cells by the ortho-cresolphthalein complexone method. A—Calibration graph for calcium determination in matrix vesicles by the ortho-cresolphthalein complexone method; B—Quantification of the level of calcium in MV, isolated from VSMC that were cultured in the normal conditions or in media with high Ca/P. The level of calcium in MV was quantified by the ortho-cresolphthalein complexone method after MV capture with anti-CD63 antibody onto a 96 well plate. Note the vesicle calcium content is dependent on the amount of vesicles plated and also on whether matrix vesicles were derived from. VSMCs treated with Ca/P.

FIG. 6 shows that GW4869 promotes calcification of human smooth muscle cells. A—VSMCs were incubated in the absence or presence of high Ca/P (2.5 mM Ca and 2.5 mM P) in 2% FBS/M199 media for 5 days and subjected to alizarin D staining Quantification shown graphically in B. Mean±SD, n=3. C—pictures of VSMCs were taken using light microscopy of alizarin-D stained VSMCs. 1.5—BSA control; 2.6–+5 mM GW4869; 3.7–+1.3% DSMO; 4.8–+1 uM Y-27632.

Figure 7:
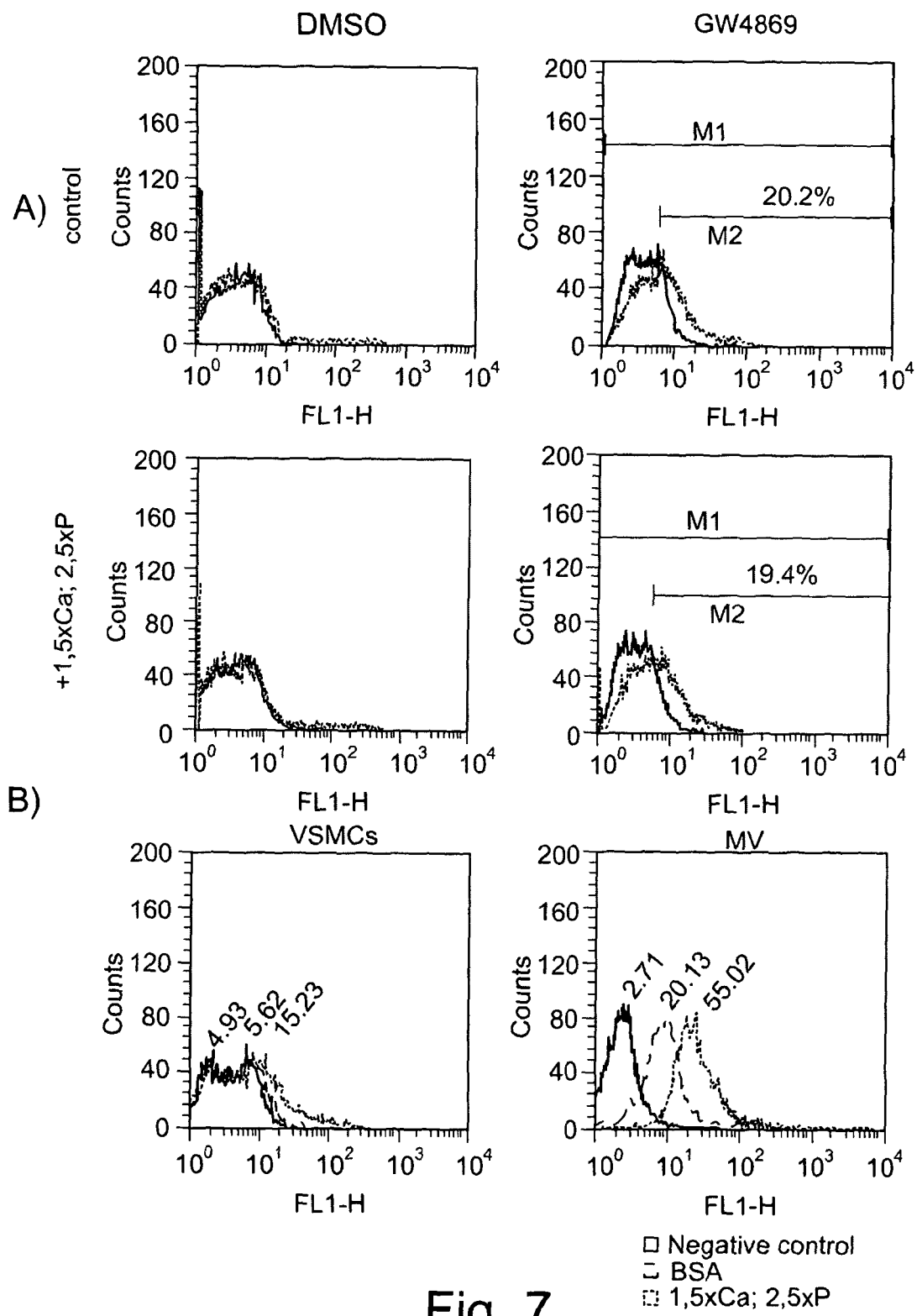

FIG. 7 shows that both high Ca and P treatment of VSMCs and inhibition of matrix vesicle release using GW4869 induce phosphatidylserine externalization and VSMCs apoptosis. A—apoptosis of VSMCs in the presence of GW4869 as detected by AnnexinV-FITC binding VSMC were treated with 5 mM GW4869 in the absence or presence of high Ca/P and the level of apoptosis was determined by phospahtidylserine externalization. Note the appearance of AnnexinV-FITC-positive VSMCs, treated with GW4869.

B—apoptosis of VSMCs and externalization of phosphatidylserine on MV in the presence of high Ca/P in the culture media. VSMCs were incubated in the presence of (2.7 mM Ca and 2.5 mM P) and probed for annexinV-FITC binding. Note the appearance of AnnexinV-FITC-positive VSMCs in response to high Ca/P treatment as detected by the shift of mean fluorensence units (up to value of 15.23). MV were isolated from VSMC culture supernatants, immobilized to beads and analysed for AnnexinV-FITC binding by flow cytometry. Note the shift of Mean fluorescence units, representing annexinV-FITC binding from 20.13 to 55.02 in response to high Ca/P treatment.

FIG. 8 shows that the matrix vesicle marker CD63 is absent in the vessel wall of a normal uncalcified aorta. However it is heavily deposited at sites of calcification in both the media and intima of aged or atherosclerotic human arteries (arrowed). This is indicative of matrix vesicle release by VSMCs at sites of calcification.

Figure 9:
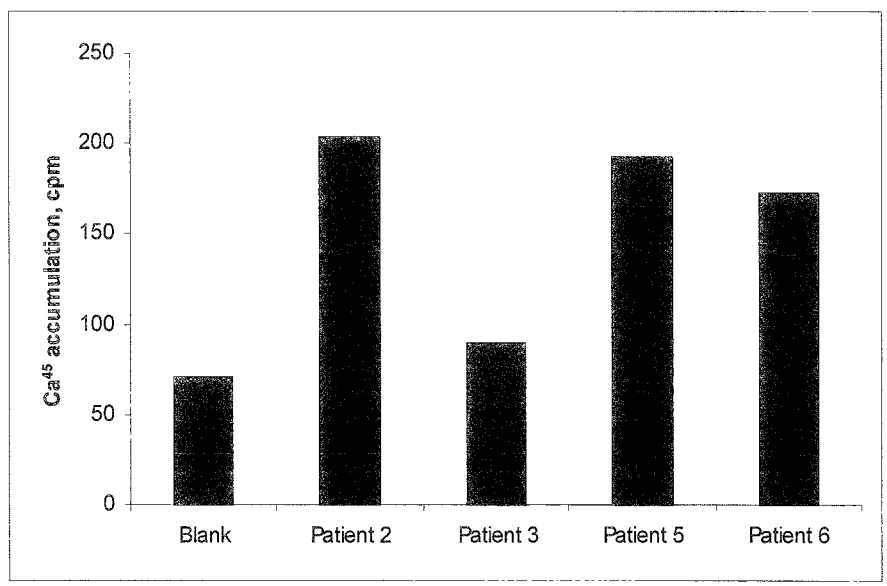

FIG. 9 shows a calcification assay on matrix vesicles that were isolated from the blood of patients on dialysis by differential ultracentrifugation. This demonstrated that matrix vesicles contained variable amounts of calcium and were capable of mediating calcification in vitro. The differences in calcification potential may reflect the different calcification states of the individual patients.

Figure 10:
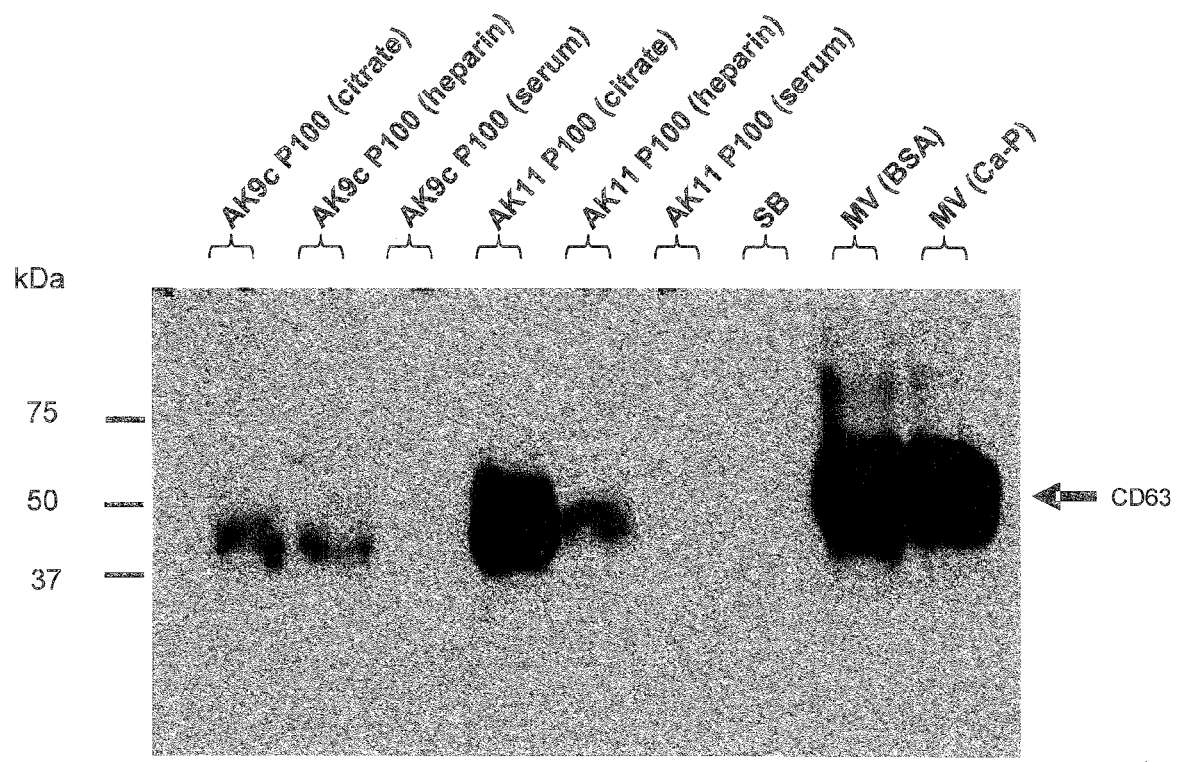

FIG. 10 shows detection of CD63 in the membrane-bound matrix vesicles isolated from the blood of a healthy individual (AK11) and a diabetes type 2 patient (AK9c).

MV pellets were isolated using ultracentrifugation. Aliquots of MV were separated by 10% SDS-PAGE and transferred to the membrane. CD63 was detected using western-blotting. AK9cP100 and AK11P100=pellets isolated from the plasma (citrate and heparin) or serum of patients with diabetes type 2 (C) or healthy control. SB=SDS-PAGE sample buffer.

Figure 11:
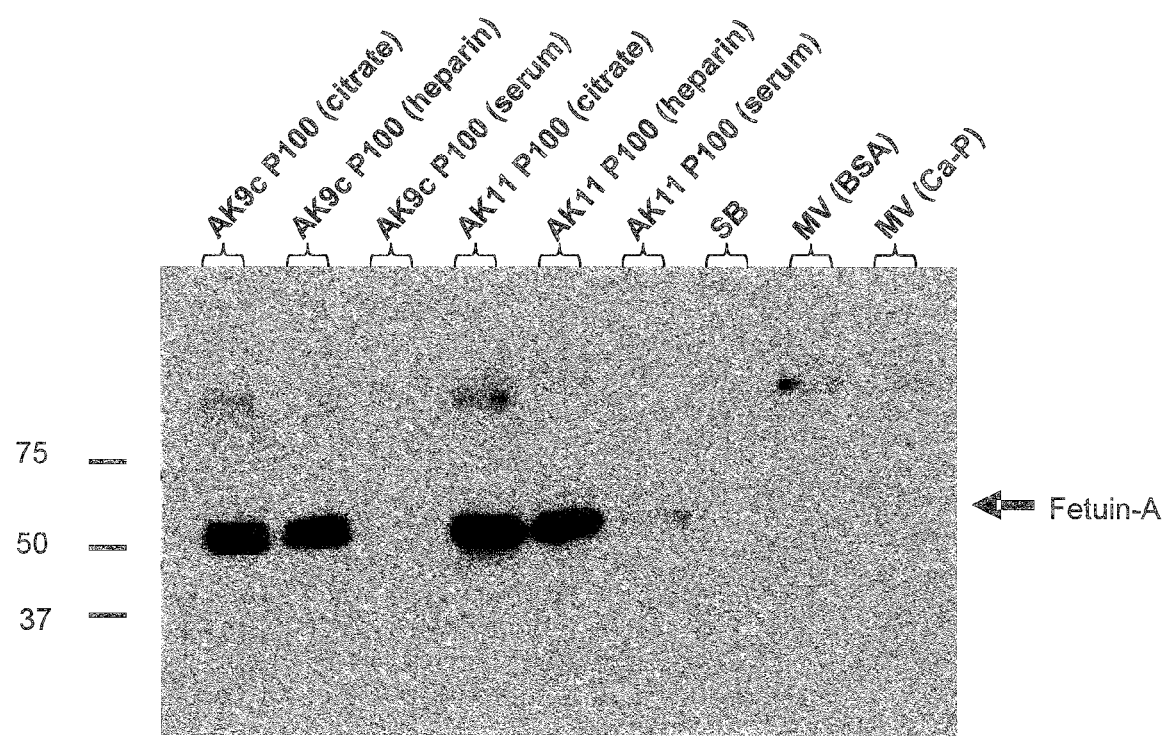

FIG. 11 shows detection of fetuin-A in the membrane-bound matrix vesicles isolated from the blood of healthy individuals (AK11) and diabetes type 2 patient (AK9c).

MV pellets were isolated using ultracentrifugation. Aliquots of MV were separated by 10% SDS-PAGE and transferred to the membrane. Fetuin-A was detected using western-blotting. AK9cP100 and AK11P100=pellets isolated from the blood samples—plasma (citrate and heparin) or serum (serum) of the patient with diabetes type 2 or healthy control, correspondingly; MV=matrix vesicles isolated from the culture media of vascular smooth muscle cells treated in control conditions (BSA) or in the presence of 2.7 mmol/L CaCl2/2.5 mmol/L NaH2PO4.

Figure 12:
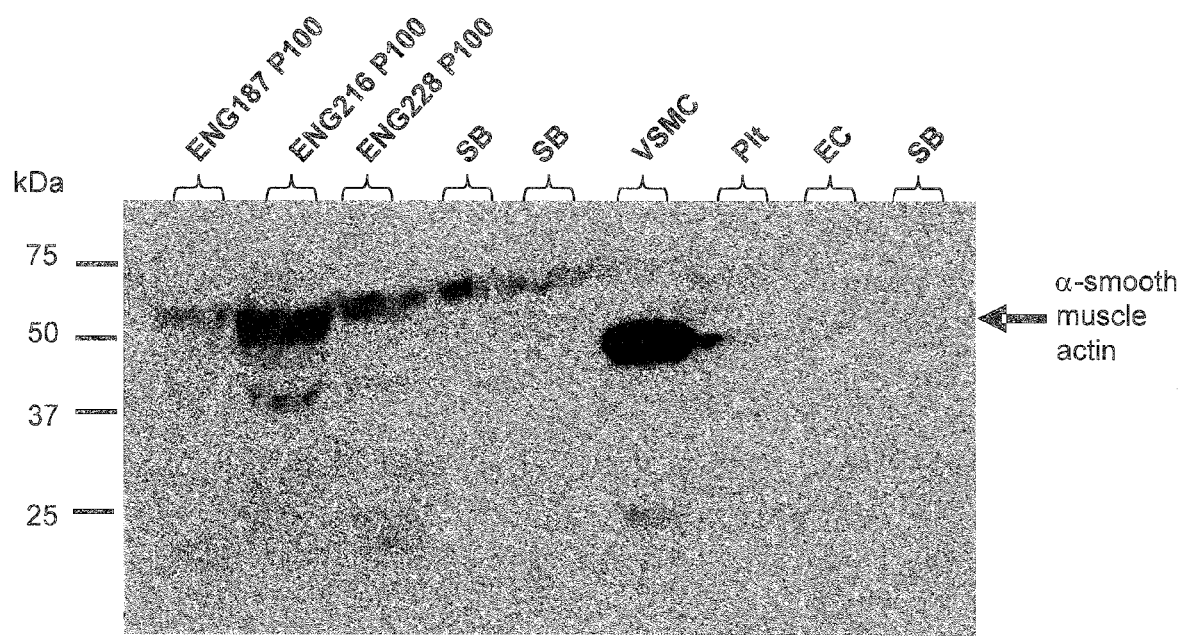
Figure 13:
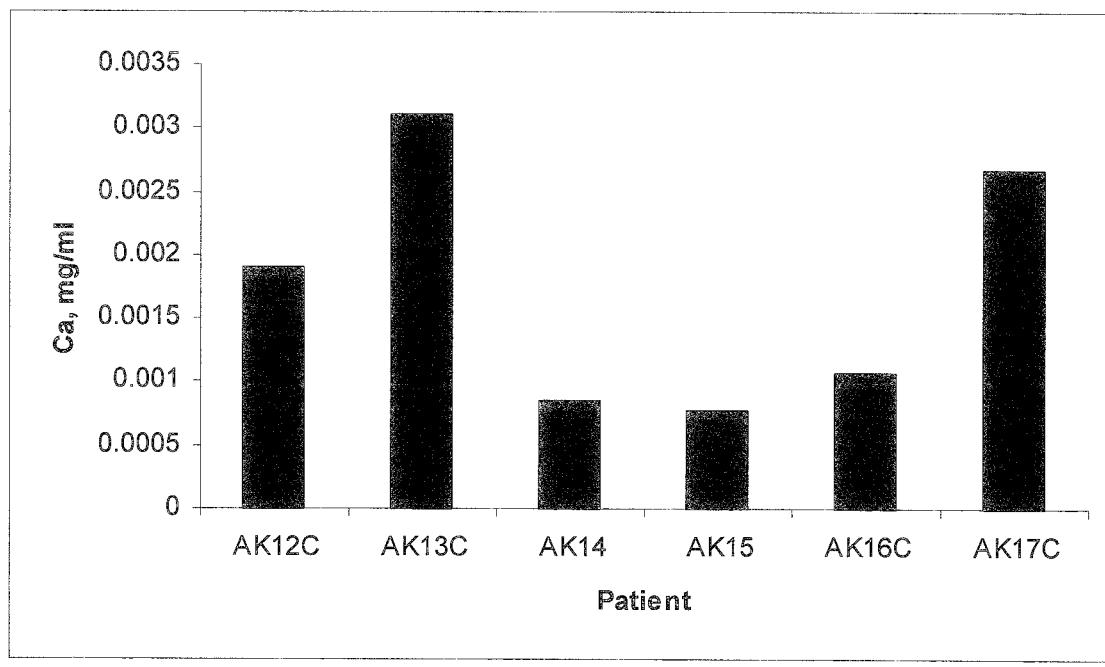

FIG. 12 shows detection of α-smooth muscle actin (α-SMA) in the matrix vesicles isolated from the blood of healthy individuals (ENG187, ENG216 and ENG228) MV pellets were isolated using ultracentrifugation. Aliquots of MV were separated by 10% SDS-PAGE and transferred to the membrane. α-SMA was detected using western-blotting. ENG187P100, ENG216P100 and ENG228P100=pellets isolated from the plasma of healthy control group. VSMCs=lysate of human smooth muscle cells; Plt=platelets microvesicles; EC=lysates of human endothelial cells; SB=SDS-PAGE sample buffer FIG. 13 shows quantitative determination of calcium in matrix vesicle pellets obtained from blood of patients with diabetes type 2 (AK12C; AK13C and AK16C); diabetes type 1 (AK17C) and healthy individuals (AK14, AK15). MV were isolated by ultracentrifugation from plasma from the blood of healthy individual and individuals with diabetes type 1 and type 2. Calcium concentration was measured by spectrophotometry using o-cresolphthalein complexone method.

Note an increased amount of a vesicular component, calcium, in the MV pellets obtained from patients with type 1 or type 2 diabetes having vascular calcification (AK12C, AK13C, AK16C, AK17C) when compared to the amount of calcium in the MV obtained from the healthy individuals (AK14, AK15).

Figure 14:
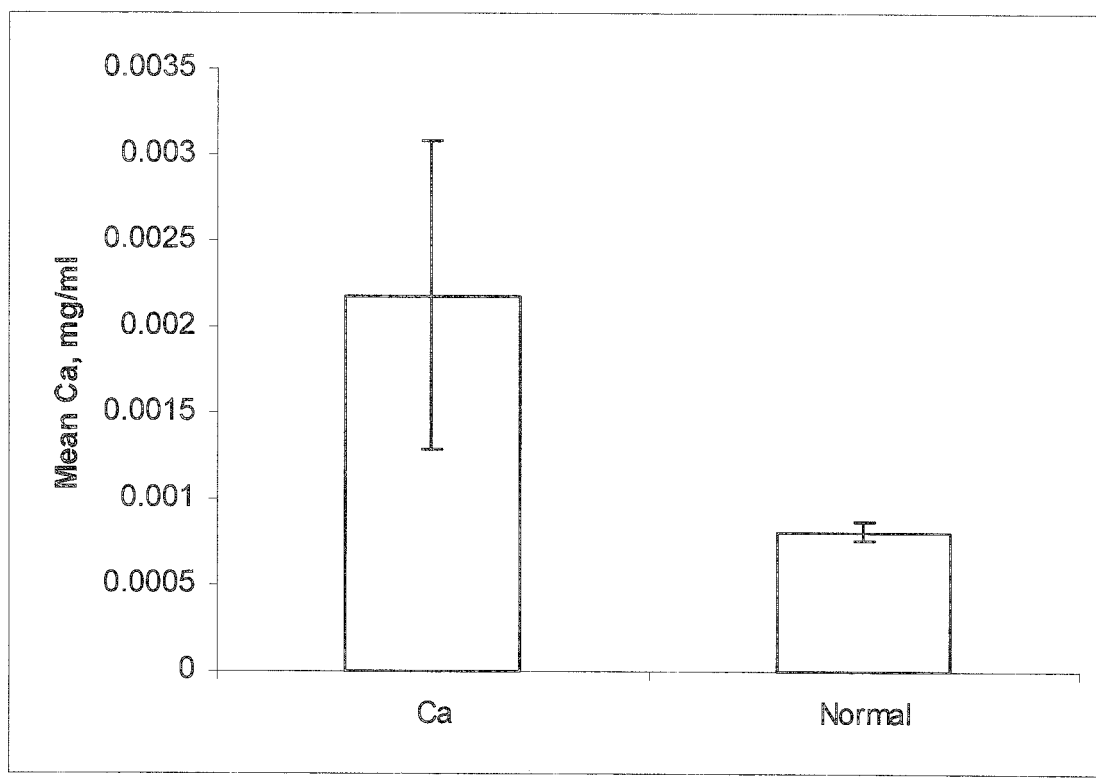

FIG. 14 shows quantitative determination of calcium in matrix vesicles pellets obtained from blood of patients with diabetes type 2 (AK12C; AK13C and AK16C); diabetes type 1 (AK17C) and healthy individuals (AK14, AK15). Mean value and standard deviation were calculated from the data presented in FIG. 13 for patients with peripheral artery vascular calcification (Ca) and healthy control (Normal). Note an increased amount of an vesicular compound, calcium, in the MV pellets obtained from the patients with 2 diabetes having vascular calcification (AK12C, AK13c, AK16c, AK17c) when compared to the amount of calcium in the MV obtained from the healthy individuals (AK14, AK15).

Figure 15:

FIG. 15 shows vascular calcification of the peripheral arteries in the lower limb of patient with diabetes type 2 was verified by plane X-ray. Lateral weight bearing foot x-ray. Patient 12C. Note vascular calcification of tibialis posterior (a) and dorsalis pedis artery (b).

MATERIAL AND METHODS

Diagnostic Assay for the Assessment of Risk of Vascular Calcification

Samples of platelet poor plasma or matrix vesicles isolated from platelet poor plasma by ultracentrifugation, are incubated in a microwell of a 96 well plate pre-coated with CD63 capture antibody. After washing the wells captured matrix vesicles are lysed in a small volume of 0.1N HCl and neutralized by 0.1N NaOH/0.1% SDS, The level of calcium is determined by the ortho-cresolphthalein complexone method. The calcium concentration is quantified by measuring the solution's absorbance at 450 nm and comparing the value obtained against a standard curve (FIG. 5A). Ca loading scores are analyzed for the association with vascular calcification which can then be verified by X-ray and/or multislice CT scanning FIG. 5B shows that the presence of calcium in matrix vesicles secreted by VSMCs can be detected. Matrix vesicles were isolated by ultracentrifugation from human VSMCs incubated under either normal or elevated calcium conditions. The vesicles were captured using CD63 specific antibodies and the calcium content determined as described above.

To improve the specificity of the test and its versatility as an indicator of active calcification processes the content of proteins that specifically accumulate in the calcifying matrix vesicles can also be measured, for example, the proteins listed in Table 3.

If appropriate the matrix vesicles may also be captured via different matrix vesicle surface protein markers in order to specifically trap VSMCs-derived MV from the sample. Examples of these are shown in Tables 1 and 2.

TABLE 1

Protein components of smooth muscle cells derived matrix vesicles used for the capture of matrix vesicles and assessment of cardiovascular risks Proteins, associated with plasma membrane suitable for capturing of vascular smooth muscle cells-derived matrix vesicles CD63
T-cadherin
CD166
Annexin A6
Cardiovascular risk factor proteins, present in smooth muscle cell derived matrix vesicles Growth arrest-specific protein 6 (Gas6)

TABLE 2

Membrane-associated proteins identified by protein mass-spectrometry to be used for capturing of VSMCs-derived matrix vesicles

| # | Protein |
|---|---|
| 1 | CD63 |
| 2 | CD9 |
| 3 | T-cadherin |
| 4 | HLA class I |
| 5 | 78 kDa glucose-regulated protein precursor - *Homo sapiens* (GRP78) |
| 6 | 94 kDa glucose-regulated protein (GRP94) |
| 7 | Transferrin receptor protein 1 |
| 8 | CD166 |
| 9 | Thy-1 |
| 10 | Phospholipid scramblase 3 |
| 11 | Sodium/potassium-transporting ATPase |
| 12 | Integrin beta-1 |
| 13 | Integrin alpha-2 |
| 14 | Integrin alpha-V |
| 15 | Integrin beta-3 |
| 16 | Integrin alpha-1 |
| 17 | Integrin alpha-4 |
| 18 | CD44 |
| 19 | Membrane glycoprotein gp140 |
| 20 | Endoglin precursor |
| 21 | Prolow-density lipoprotein receptor-related protein 1 |
| 22 | Intercellular adhesion molecule 1 |
| 23 | Cation-independent mannose-6-phosphate receptor |
| 24 | Transmembrane emp24 domain-containing protein 10 |
| 25 | CD59 glycoprotein |
| 26 | Poliovirus receptor-related protein 2 |
| 27 | Guanine nucleotide-binding protein subunit alpha-11 |
| 28 | Transgelin-2 |
| 29 | Aminopeptidase B |
| 30 | Importin-7 |
| 31 | Reticulon-4 |
| 32 | Sideroflexin-3 |
| 33 | ADP/ATP translocase 1 |
| 34 | Erythrocyte band 7 integral membrane protein |
| 35 | Nicastrin |
| 36 | CD97 |
| 37 | ADAM 9 |
| 38 | Melanoma-associated antigen p97 (CD228) |
| 39 | Sulfate transporter |
| 40 | Choline transporter-like protein 1 (CD92) |
| 41 | Vesicle-associated membrane protein 3 |
| 42 | Ezrin |
| 43 | Golgin subfamily A member 7 |
| 44 | CD109 |

Example 1

VSMCs Matrix Vesicles are Exosomal Like Vesicles

To explore the possible exosomal origin of VSMCs vesicles the presence of known exosomal markers was analysed on VSMCs plasma and matrix vesicle membranes. Exosomal markers CD9, CD63 and also MHC class I molecules were abundantly presented both on VSMCs and vesicle membrane surfaces (FIG. 3B). Moreover matrix vesicles were considerably enriched with tetraspans of CD9 and CD63 compared with VSMCs (FIG. 3C). Neither cells nor matrix vesicles expressed MHC class II molecules (data not shown).

To determine whether MV originated from an intracellular compartment the presence of lysosomal markers, LAMP-1 and LAMP-2, on the surface of VSMCs and MV was analysed. LAMP-1 was detected both on VSMCs plasma membranes and MV (data not shown), whereas LAMP-2 was present on MV only. Western-blotting showed little enrichment of LAMP-2 in matrix vesicles. Since LAMP-1 and LAMP-2 are lysosomal markers, the presence of the lysosomal enzyme, cathepsin D was examined. It was found that MV do not contain cathepsin D (FIG. 3C).

We were also able to detect acetylcholinesterase activities in MV (FIG. 3D), a feature which also consistent with exosomal nature of these vesicles (Johnstone et al., 1987).

FIG. 2 shows that CD63 matrix vesicles can be isolated from human blood indicating that these matrix vesicles are present in the circulation.

Example 2

Quantitative Assessment of Calcium Load Inside the Matrix Vesicles (Exosomes), Derived from VSMCs Cultures The diagnostic test employs highly specific murine monoclonal antibodies recognizing a matrix vesicle biomarker CD63 as capture antibodies as described above.

As described above, FIG. 5 shows that the calcium load is higher in matrix vesicles, isolated from VSMCs, exposed to high calcium/high phosphate (model of pathological conditions) than in matrix vesicles, isolated from VSMCs treated in normal conditions.

The measurements of calcium inside the calcifying matrix vesicles can be a clinically validated diagnostic tool and predicts individual risk of vascular calcification and the development cardiovascular disease.

Example 3

Analysis of VSMCs Matrix Vesicles

We have shown that vascular calcification is initiated in matrix-vesicles (MV) released from vascular smooth muscle cells (VSMCs) (Reynolds, J. L., et al (2004) J. Am. Soc. Nephrol. 15 (11) 2857-67). These MV are enriched in calcium and their release is induced by calcium. Under normal conditions matrix vesicles are loaded with inhibitors such as matrix gamma-carboxyglutamic acid protein (MGP) and fetuin-A and do not calcify. However a local or systemic mineral imbalance leads to the perturbation of production of these inhibitors and leads to a phenotypic transformation of VSMCs into osteo/chondrocytic-like cells that produce calcifying MV that contain higher levels of calcium and in some cases, calcium phosphate crystals.

The proteomic composition of VSMCs-derived MV isolated by ultracentrifugation from the cell media has been characterised and found to be enriched in around 500 proteins, of which a number are listed in Table 3. Using Western blotting we confirmed an enrichment of the exosomal marker CD63, and T-cadherin, a protein abundantly expressed in the cardiovascular system and neurons. It has also been shown that the treatment of VSMCs with elevated calcium/phosphate modifies the protein composition of the released MV (data not shown).

This data suggests that VSMCs in response to a mineral imbalance (high calcium and phosphate in the serum) secrete MV which contain calcium phosphate crystals and have increased levels of several marker proteins indicative of VSMCs stress (Table 2). VSMCs-derived MV have been captured on CD63-antibodies immobilized on 96 well plates and the calcium load measured (FIG. 5).

As can be seen the calcium load of MV derived from Ca/P-treated VSMCs was higher than the Ca load of MV derived from untreated VSMCs.

MV have been shown to be present in the circulation. Using Western blotting CD63 has been detected in these circulating vesicles, isolated from platelet-free plasma by ultracentrifugation (FIG. 2)

TABLE 3

Proteins altered in matrix vesicles in response to Ca/P treatment of vascular smooth muscle cells as possible indicators of cardiovascular risk

| # | Protein |
|---|---|
| 1 | calreticulin |
| 2 | reticulocalbin 1 |
| 3 | Calumenin |
| 4 | Stromal cell-derived factor 4 |
| 5 | Calcium-binding protein p22 |
| 6 | Caldesmon |
| 7 | S100 calcium binding protein A11 |
| 8 | S100 calcium binding protein A8 |
| 9 | Plasma membrane calcium-transporting ATPase 1 |
| 10 | VAMP3 vesicle-associated membrane protein 3 |
| 11 | Rab-5C |
| 12 | Rab7A |
| 13 | Programmed cell death 6-interacting protein |
| 14 | Small VCP/p97-interacting protein |
| 15 | PSMB4 proteasome subunit |
| 16 | PSMD13 26S subunit |
| 17 | Annexin A1 |
| 18 | Annexin A2 |
| 19 | Annexin A5 |
| 20 | Annexin A6 |
| 21 | VKORC1 vitamin K epoxide reductase complex, subunit 1 |
| 22 | Growth arrest-specific protein 6 (Gas6) |
| 23 | CCDC80 coiled-coil domain containing 80 |
| 24 | Sodium/potassium-transporting ATPase subunit alpha-1 |
| 25 | Microtubule-associated protein 1B |
| 26 | Macrophage migration inhibitory factor |
| 27 | Aminopeptidase N |
| 28 | Plasminogen activator inhibitor 1 |
| 29 | Calpain-1 |
| 30 | Guanine nucleotide-binding protein G(i), alpha-2 subunit |
| 31 | Thyroxine-binding globulin precursor |
| 32 | heat shock protein 90 kDa (HSP90) class A member 1 |
| 33 | heat shock protein 90 kDa (HSP90) class B member 1 |
| 34 | heat shock protein 90 kDa alpha class B member 3 |
| 35 | heat shock 70 kDa protein 8 |
| 36 | heat shock 70 kDa |
| 37 | heat shock 70 kDa protein 1B |
| 38 | heat shock 27 kDa protein 1 |
| 39 | heat shock 10 kDa protein 1 (chaperonin 10) |
| 40 | ST13 suppression of tumorigenicity 13 |
| 41 | t-complex 1 |
| 42 | tubulin folding cofactor A |
| 43 | chaperonin containing TCP1, subunit 6A |
| 44 | PDIA1 Protein disulfide-isomerase |
| 45 | 60S ribosomal protein L4 |
| 46 | 60S ribosomal protein L12 |
| 47 | 60S ribosomal protein L13a |
| 48 | 60S ribosomal protein L27a |
| 49 | 40S ribosomal protein S14 |
| 50 | Nucleolin |
| 51 | Reticulocalbin-1 |
| 52 | Neurogenic locus notch homolog protein 2 |
| 53 | Tumor necrosis factor-inducible gene 6 protein |
| 54 | Splicing factor, arginine/serine-rich 3 |
| 55 | Neuronal calcium sensor 1 |
| 56 | Tyrosine-protein kinase receptor UFO |
| 57 | Small nuclear ribonucleoprotein Sm D2 |
| 58 | Tropomyosin aipha-3 chain |
| 59 | Vacuolar protein sorting-associated protein 37C |

Many proteins have previously been identified as enriched in exosomes, for example, integrins, Rab proteins, annexins. In addition to exosomal proteins there are a number of proteins that have previously been identified in chondrocyte MV including collagens, annexins, Na/K-exchanging APTase.

Using WB we have shown that these proteins are enriched in VSMCs-derived MV and many are specific to MV and not found in apoptotic bodies (AB). Western blotting has shown that CD9, CD63 and T-cadherin are enriched in MV in comparison with apoptotic bodies and whole cell lysates. In addition, we found many proteins, again in common with exosomes, that are involved in cell adhesion, membrane fusion and exosome biogenesis further supporting the notion that calcifying MV secreted by VSMCs are biochemically similar to previously described exosomes released by many cell types into the extracellular environment.

It was shown that the exosomes from different cells contain numerous cytosolic proteins, which could be trapped in the exosome during its biogenesis (Thery et al., 2002). We analyzed the presence of cytosolic proteins in MV using western blot. As shown on picture 3C, MV were positive for alpha smooth muscle actin and vinculin, but negative for HSP70.

The above studies suggested that the MV released by VSMCs at sites of calcification are potentially of exosomal origin. To investigate this we performed immunohistochemisty on normal and calcified human aortic and carotid artery samples (FIG. 8). This showed that in the normal vessel wall CD63 staining was not present. However in calcified vessels CD63 staining was extensive and co-localized in a punctate pattern with von Kossa positive areas of calcification. This staining appeared to be specific as markers of lysosomes such as Lamp2 were not present suggesting the vesicles were derived from living VSMCs.

In a search for more evidence for a MVB origin of MV we performed EM on vessel rings obtained from dialysis patients who undergo extensive and rapid medial vascular calcification. This showed the presence of MVB in VSMCs derived from calcified patients however these were not observed in VSMCs of the normal vessel wall (data not shown).

Example 4

Inhibition of Exosomal Release Affects Calcification In Vitro and Influence VSMCs Survival We have shown earlier that vascular calcification is initiated in nodules by release of apoptotic bodies (AB) and in matrix-vesicles (MV) from VSMCs by unknown mechanisms. According to the data above, the matrix vesicles have an endosomal origin and their release could be blocked by exosome-release inhibitor, GW4869 therefore we tested the effect of GW4869 on VSMCs calcification in vitro.

VSMCs were cultured in the presence or absence of GW4869 and with or without high Ca and P in the media containing 2% serum for 5 days. Control cells did not show any evidence of calcification (FIG. 6A). Treatment of VSMCs with a selective inhibitor of the ROCK (Y 27632), blocking membrane vesicle shedding from the plasma membrane, also had no effect (FIG. 6A). In contrast, VSMCs treated with GW4869 in the presence of raised extracellular concentrations of Ca and P calcified extensively (FIG. 6A). This was accompanied by a dramatic reduction in the number of VSMCs in wells, treated with GW4869. We suggested that inhibition of exosome release could induce an apoptosis in VSMCs, which, in turn, leads to the reduction of the cell number and rapid calcification. Indeed, VSMCs exposed to GW4869 undergo apoptosis in 24 hours (FIG. 7A).

High Ca and P alone is able to induce an apoptosis of VSMCs in the serum free media (FIG. 7B). We therefore compared an effect of GW4869 on cell survival in the presence of raised extracellular concentrations of Ca and P in the media containing 2% serum. Interestingly, apoptosis of VSMCs was not increased by the presence of high Ca and P (FIG. 7A). This suggests that cytotoxic effect of inhibition of vesicle release can occur under normal physiological conditions.

Membrane vesicles can be generated by membrane blebbing from the plasma membrane, so we tested whether incubation of VSMCs in the presence of raised extracellular concentrations of Ca and P could potentially induces plasma membrane blebbing and modify matrix vesicle composition. We compared annexin V binding to the matrix vesicles released in serum-free conditions with MV released by VSMCs treated with raised extracellular concentrations of Ca and P in the media (FIG. 7). Surprisingly, the matrix vesicles released under control conditions were annexin V-FITC positive. The treatment with high Ca and P resulted in a decrease of annexin V-FITC binding to MV (FIG. 7B, above). At the same time they were completely CD63-positive, pointing out their endosomal origin (data not shown). Our data suggest that in the presence of elevated Ca and P VSMC-released MV may have an endosomal origin but a different phospholipids/protein composition.

The date presented here suggest that inhibition of exosome release by GW4869 affects the calcification of VSMCs at least by the induction of cell apoptosis.

Analysis of matrix vesicles by EM, flow cytometry and western=blotting has revealed that matrix vesicles display a unique set of proteins compared with total cell membranes but are similar to exosomes. Taken together, these data suggest that the calcifying matrix vesicles have an endosomal origin. Inhibition of exosome release causes a dramatic redistribution of exosomal markers and accumulation of fetuin-A in the endosomal compartment and induces apoptosis followed by rapid calcification. Calcification in vivo correlates with the accumulation of CD63-positive matrix vesicles in the vessel wall.

Example 5

Detection of Calcifying Matrix Vesicles in Plasma of Patients Undergoing Dialysis FIG. 9 shows the presence of calcifying matrix vesicles in the blood of patients suffering from chronic kidney disease and undergoing regular dialysis. Matrix vesicles were isolated from platelet free citrated plasma by ultracentrifugation. An aliquot of the isolated matrix vesicles was incubated with $Ca^{45}$ under calcifying conditions ($Ca^{45}$ [50000 cpm] 2.2 mM $CaCl_2$, 1.6 mM $KH_2PO_4$, 1 mM $MgCl_2$, 85 mM NaCl, 15 mMKcl, 10 mM $NaHCO_3$, 50 mM N-Tris(hydroxymethyl)methyl-2-aminoehanesulfonic acid at 37° C. for 24 hours) and $Ca^{45}$ uptake measured. Accumulation of $Ca^{45}$ in the matrix vesicles indicates that the matrix vesicles are able to calcify and therefore must contain pre-formed calcium phosphate salts which serve as nucleation sites. As can be seen, the amount of $Ca^{45}$ uptake in the patients suffering from chronic renal disease is considerably higher than that seen in the control indicating that these patients have an increased risk of developing vascular calcification.

Example 6

Detection of Calcifying Matrix Vesicles in Blood from Patients Suffering from Vascular Pathologies Associated with Increased Calcification I. Obtaining a Sample Comprising Matrix Vesicles from the Blood of Individuals.

The matrix vesicles were isolated from the blood samples by ultracentrifugation.

1. Blood was collected in BD Vacutainer Serum tubes (BD Bioscience) or BD Vacutainer Citrate Tubes (buffered with 32% sodium citrate, BD Bioscience).

2. Blood samples were subjected to centrifugation at 3200 rpm in a Thermo Scientific Heraeus Multifuge 3SR+ centrifuge (rotor Sorvall 75006441K) for 15 min at 4° C. Supernatant (plasma or serum; volume 2.5-4 mL) was carefully transferred to the ultracentrifugation tubes (Beckman Coulter) and the pellet was discarded.

3. Serum and plasma samples were subjected to centrifugation at 45,000 rpm (100,000×g) for 90 minutes at 4° C. (Beckman Coulter Optima Max Unitracentrifuge).

4. Pellets were resuspended in 5 ml of calcium/magnesium-free phosphate buffer saline (PBS, Invitrogen) and then were subjected to centrifugation at 45,000 rpm (100,000×g) for 90 minutes at 4° C. (Beckman Coulter Optima Max Unitracentrifuge).

5. Pellets were resuspended in 0.5 mL of PBS and transferred to new ultracentrifugation tubes and then were subjected to centrifugation at 47,000 rpm (100,000×g) for 90 minutes at 4° C. (Beckman Coulter Optima Max Unitracentrifuge).

Supernatant was discarded and pellets (MVs pellets) were kept at −80° C.

II Measuring the Total Amount of Matrix Vesicles Obtained from the Blood.

1. MV pellets were kept at −80° C. and resuspended in small volume of calcium/magnesium-free PBS (Sigma)

2. Protein concentration was determined using DC protein assay (BioRad) as per the manufacturers instructions.

III. Measuring the Amount of Vesicular Compound (Calcium) in Pellets Obtained from the Blood The level of calcium is determined by o-Cresolphthalein Complexone method.

1. Samples of matrix vesicles pellets obtained from blood samples (plasma or serum) by ultracentrifugation, were incubated in a 96 well plate E a small volume (55 µl) of 0.1M HCl for 30 min at room temperature.

2. Samples were mixed with 25 µl of de-ionized water, 10 µl of o-Cresolphthalein Complexone solution (0.1% o-Cresolphthalein Complexone–50 µg of o-Cresolphthalein Complexone dissolved in 36 mL of $H_2O$ and 14 mL of ammonia buffer were added) and 200 µl of ammonia buffer (0.24% $NH_4Cl$, 5% $NH_4OH$, pH 10.5).

3. The calcium concentration is quantified by measuring the solution's absorbance at 450 nm and comparing the value obtained against a standard curve.

IV. Measuring the Amount of Vesicular Compounds in Matrix Vesicles Obtained from the Blood Using Western Blotting 1. MV pellets were kept at −80 C and resuspended in small volume of calcium/magnesium-free PBS (Sigma). Protein concentration of lysates was determined using DC protein assay (Bio-Rad).

2. An aliquots of MV samples containing 5-50 µg of total protein were separated on 10% SDS-PAGE and transferred to Immobilon-P membrane (Millipore) using semi-dry transfer cell (Bio-Rad).

3. The membrane was blocked in blocking buffer (PS containing 5% dry milk and 0.05% Tween-20) and then incubated with primary antibody for CD63, fetuin-A or α-smooth muscle actin.

4. The membrane was washed in blocking buffer and incubated with horseradish peroxidase-conjugated secondary antibody (General Electric, 1:5000) diluted in blocking buffer, washed in PBS containing 0.05% tween-20 and visualized using the ECL or ECL+ system (Amersham).

TABLE I

Clinical parameters of the healthy controls and patients with established peripheral artery calcification (foot and ankle calcification) established by x-ray.

| Patient ID | Gender | Age | Condition | Corrected Calcium 2.15-2.6 mmol/l | Inorganic Phosphate 0.8-1.4 mmol/l |
|---|---|---|---|---|---|
| AK9C | male | 51 | diabetes type 2 | 2.31 | 0.83 |
| AK11 | female | 41 | healthy | | Not done |
| AK12C | male | 53 | diabetes type 2 | 2.34 | 1.36 |
| AK13C | male | 72 | diabetes type 2 | 2.23 | 1.4 |
| AK14 | male | 32 | healthy | Not done | Not done |
| AK15 | female | 31 | healthy | Not done | Not done |
| AK16C | male | 62 | diabetes type 2 | 2.15 | 1.54 H |
| AK17C | female | 65 | diabetes type 1 | 2.32 | 0.95 |

Results

Membrane-bound matrix vesicles were isolated from the blood of healthy individuals and individuals with vascular pathologies associated with increased calcification (chronic kidney disorder, hypertension, age and diabetes type 2 patients). It was observed that matrix vesicles obtained from both healthy individuals and individuals with vascular pathologies were enriched with CD63 and fetuin-A see FIGS. 10, 11. CD63 and fetuin-A were detected by western blotting.

FIG. 12 shows the presence of the smooth muscle cell marker a-SM actin in the blood-derived MV from healthy individuals indicating that MV are present in blood of these individuals.

The amount of the vesicular compound calcium present in the MV pellets isolated by ultracentrifugation from blood samples (plasma and serum) of healthy individuals and individuals with diabetes type 1 or diabetes type 2 was measured using spectrophotometry as described in Protocol III above. FIGS. 13 and 14 shows that individuals who have diabetes type 1 or diabetes type 2 have significantly higher levels of calcium in the isolated matrix vesicles than healthy individuals.

A correlation between the level of the vesicular compound, calcium in the blood-derived MV pellets and the individual risk of having vascular calcification was identified (FIGS. 13 and 14). Patients with diabetes type 1 and diabetes type 2 were characterized by extensive peripheral artery vascular calcification see FIG. 15. Note that an increased amount of the vesicular compound, calcium correlated with the risk of having vascular calcification in the individuals with diabetes type 2 and type 1 when compared to the normal range seen in healthy individuals (FIGS. 13 and 14). The diabetes type 2 patients had an identifiable level of vascular calcification as established by plane X-ray analysis (FIG. 15).

The invention claimed is:

1. An assay for identifying an individual having or at risk of developing vascular calcification, said assay comprising the steps of:
   obtaining a blood sample from said individual;
   isolating vascular smooth muscle cell-derived matrix vesicles from the blood sample using antibodies directed to a vascular smooth muscle cell membrane-associated protein;
   measuring the level of a vesicular compound associated with the vascular smooth muscle cell-derived matrix vesicles isolated from the blood sample, the vesicular compound comprising calcium or a calcium phosphate salt; and identifying the individual as having or at risk of developing vascular calcification if the individual has an increased level of said compound compared to a healthy control.

2. The assay according to claim 1 wherein the individual is a human.

3. The assay according to claim 1, wherein the individual is an individual suffering from a chronic renal disorder or from type 2 diabetes.

4. The assay according to claim 1, wherein the vesicular compound further comprises at least one of, hydroxyapatite, a calcium salt, a phosphate salt, or at least one protein selected from Gas6/Axl; Microtubule-associated protein IB; Thy-1 membrane glycoprotein; 60S ribosomal protein L30, L27a; Prohibitin; Proteasome subunit beta type-4; Elongation factor 1-delta; Gremlin-1; 14-3-3 protein beta/alpha; COP9 signalosome complex subunit CSN4; Ezrin; Programmed cell death 6-interacting protein; CD 109; Protein kinase C delta-binding protein; Calmodulin; Nucleolin, PAI-1, MMP-14.

5. The assay according to claim 4, wherein the compound is one or more of calcium, hydroxyapatite, a calcium phosphate salt or Growth arrest-specific protein 6.

6. The assay according to claim 1, wherein the compound is an intra-vesicular compound.

7. The assay according to claim 1, wherein the matrix vesicles are isolated by ultracentrifugation.

8. The assay according to claim 1, wherein the antibody is selected from an antibody against CD63, T-cadherin, CD 166 or Annexin A6.

9. The assay according to claim 1, wherein the level of the vesicular compound is measured using spectrophotometry.

10. A method of identifying an individual having or at risk of developing vascular calcification comprising:
  i) obtaining a blood sample isolated from said individual;
  ii) isolating vascular smooth muscle cell-derived matrix vesicles from the blood sample using antibodies directed to a vascular smooth muscle cell membrane-associated protein;
  iii) measuring the level of a vesicular compound associated with the vascular smooth muscle cell-derived matrix vesicles isolated from said blood sample, the vesicular compound comprising calcium or a calcium phosphate salt;
  wherein an increased level of said compound compared to a healthy control indicates that the individual has or is at risk of developing vascular calcification.

11. The method according to claim 10 wherein the individual is a human.

12. The method according to claim 10, wherein the individual is a patient suffering from a chronic renal disorder or artherosclerosis or type 2 diabetes.

13. The method according claim 10, wherein the vesicular compound further comprises at least one of, hydroxyapatite, a calcium salt, a phosphate salt, or at least one protein selected from Gas6; Microtubule-associated protein I B; Thy-1 membrane glycoprotein; 60S ribosomal protein L30, L27a; Prohibitin; Proteasome subunit beta type-4; Elongation factor 1-delta; Gremlin-1; 14-3-3 protein beta/alpha; COP9 signalosome complex subunit CSN4; Ezrin; Programmed cell death 6-interacting protein; CD109; Protein kinase C delta-binding protein; Calmodulin; Nucleolin, PAI-1, MMP-14.

14. The method according to claim 13, wherein the compound is one or more of calcium, hydroxyapatite, a calcium phosphate salt or Growth arrest-specific protein 6.

15. The method according to claim 10 wherein the compound is an intra-vesicular compound.

16. The method according to claim 10, wherein the matrix vesicles are isolated by ultracentrifugation.

17. The method according to claim 10, wherein the antibody is selected from an antibody against CD63, T-cadherin, CD 166 or Annexin A6.

18. The method according to claim 10, wherein the level of the vesicular compound is measured using spectrophotometry.

* * * * *